(12) United States Patent
De Kock et al.

(10) Patent No.: US 11,147,964 B2
(45) Date of Patent: Oct. 19, 2021

(54) SUBCUTANEOUS LEAD FIXATION MEMBER

(71) Applicant: CARDIAC PACEMAKERS, INC., St. Paul, MN (US)

(72) Inventors: Andrew L. De Kock, Ham Lake, MN (US); G. Shantanu Reddy, Minneapolis, MN (US); Peter Hall, Andover, MN (US); Christopher Alan Fuhs, Roseville, MN (US); Bryan Peter Nelson, Woodbury, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 78 days.

(21) Appl. No.: 16/390,571

(22) Filed: Apr. 22, 2019

(65) Prior Publication Data
US 2019/0321624 A1    Oct. 24, 2019

Related U.S. Application Data

(60) Provisional application No. 62/661,589, filed on Apr. 23, 2018.

(51) Int. Cl.
*A61N 1/39*    (2006.01)
*A61N 1/375*   (2006.01)
(Continued)

(52) U.S. Cl.
CPC ........... *A61N 1/0504* (2013.01); *A61N 1/057* (2013.01); *A61N 1/0563* (2013.01);
(Continued)

(58) Field of Classification Search
CPC .... A61N 1/0504; A61N 1/0563; A61N 1/057; A61N 1/37518; A61N 1/3752;
(Continued)

(56) References Cited

U.S. PATENT DOCUMENTS 4,137,919 A * 2/1979 Farin ................. A61B 18/1442
219/234
4,683,895 A * 8/1987 Pohndorf ........... A61B 17/0644
248/505
(Continued)

FOREIGN PATENT DOCUMENTS

EP      0085967 A1    8/1983
WO   2012151356 A1   11/2012

OTHER PUBLICATIONS

Darrat et al; "Single Incision Technique for Placement of Subcutaneous Implantable Cardioverter Defibrillators," http://abstractsonline.com/pp8/, accessed May 14, 2018.
(Continued)

*Primary Examiner* — Carl H Layno
*Assistant Examiner* — Anh-Khoa N Dinh
(74) *Attorney, Agent, or Firm* — Seager, Tufte & Wickhem LLP

(57) ABSTRACT

Retainer devices and methods are configured for securing medical devices subcutaneously in a patient. The retainer device may include first and second arms connected by a bridge, the retainer clip configured to move between a first orientation in which lower surfaces of the first and second arms face each other, and a second orientation in which the first and second arms extend laterally from opposite sides of the bridge, wherein the clip is biased in the second orientation. Another example includes a coil and delivery device in which the delivery device holds the coil in a general straight configuration until release; when released the coil wraps about a medical device and holds the device to the subcutaneous tissue.

19 Claims, 21 Drawing Sheets

(51) Int. Cl.
*A61N 1/05* (2006.01)
*A61B 17/068* (2006.01)
*A61B 17/064* (2006.01)

(52) U.S. Cl.
CPC ........ *A61N 1/3752* (2013.01); *A61N 1/37518* (2017.08); *A61N 1/3962* (2013.01); *A61N 2001/058* (2013.01)

(58) Field of Classification Search
CPC ............ A61N 1/3962; A61N 2001/058; A61B 5/0254; A61B 2017/0649; A61B 2017/0645; A61B 17/068; A61B 17/064
See application file for complete search history.

(56) References Cited

U.S. PATENT DOCUMENTS

| | | | |
|---|---|---|---|
| 4,716,888 | A | 1/1988 | Wesner |
| 6,647,292 | B1 | 11/2003 | Bardy et al. |
| 6,721,597 | B1 | 4/2004 | Bardy et al. |
| 7,149,575 | B2 | 12/2006 | Ostroff et al. |
| 7,194,302 | B2 | 3/2007 | Bardy et al. |
| 7,493,175 | B2 | 2/2009 | Cates et al. |
| 7,655,014 | B2 | 2/2010 | Ko et al. |
| 8,019,443 | B2 | 9/2011 | Schleicher et al. |
| 8,244,377 | B1 | 8/2012 | Pianca et al. |
| 8,285,397 | B2 | 10/2012 | Grandhe |
| 8,332,043 | B1 | 12/2012 | Jaax et al. |
| 9,610,435 | B2 | 4/2017 | Schleicher et al. |
| 9,981,121 | B2 | 5/2018 | Seifert et al. |
| 2004/0230279 | A1 | 11/2004 | Cates et al. |
| 2004/0230282 | A1 | 11/2004 | Cates et al. |
| 2006/0100649 | A1* | 5/2006 | Hart ........................ A61B 17/08 606/157 |
| 2007/0255295 | A1 | 11/2007 | Starkebaum et al. |
| 2008/0208247 | A1 | 8/2008 | Rutten et al. |
| 2009/0125059 | A1 | 5/2009 | Verzal et al. |
| 2009/0175016 | A1* | 7/2009 | Legen ................. H01L 23/3672 361/787 |
| 2009/0210043 | A1 | 8/2009 | Reddy |
| 2010/0131036 | A1 | 5/2010 | Geistert et al. |
| 2010/0179571 | A1* | 7/2010 | Voss ................... A61B 17/0057 606/142 |
| 2010/0256696 | A1 | 10/2010 | Schleicher et al. |
| 2011/0054580 | A1 | 3/2011 | Desai et al. |
| 2011/0054581 | A1 | 3/2011 | Desai et al. |
| 2011/0288618 | A1* | 11/2011 | Glen .................... A61N 1/0558 607/116 |
| 2012/0029335 | A1 | 2/2012 | Sudam et al. |
| 2012/0059394 | A1* | 3/2012 | Brenner ............... A61B 17/122 606/142 |
| 2013/0131767 | A1 | 5/2013 | Desai et al. |
| 2014/0144580 | A1 | 5/2014 | Desai et al. |
| 2014/0194963 | A1 | 7/2014 | Desai et al. |
| 2014/0330248 | A1 | 11/2014 | Thompson-Nauman et al. |
| 2014/0330327 | A1 | 11/2014 | Thompson-Nauman et al. |
| 2015/0343199 | A1 | 12/2015 | Wechter et al. |
| 2015/0352352 | A1 | 12/2015 | Soltis et al. |
| 2016/0143643 | A1 | 5/2016 | Smith et al. |
| 2016/0339233 | A1 | 11/2016 | De Kock et al. |
| 2017/0020551 | A1 | 1/2017 | Reddy et al. |
| 2017/0021159 | A1 | 1/2017 | Reddy et al. |
| 2017/0095657 | A1 | 4/2017 | Reddy et al. |
| 2017/0319845 | A1 | 11/2017 | De Kock et al. |
| 2017/0319864 | A1 | 11/2017 | De Kock et al. |
| 2018/0036527 | A1 | 2/2018 | Reddy et al. |
| 2018/0036547 | A1 | 2/2018 | Reddy |
| 2018/0078252 | A1 | 3/2018 | Sato |
| 2018/0133458 | A1 | 5/2018 | Foster et al. |
| 2018/0133462 | A1 | 5/2018 | Reddy |
| 2018/0133463 | A1 | 5/2018 | Reddy |
| 2018/0133494 | A1 | 5/2018 | Reddy |
| 2018/0169384 | A1 | 6/2018 | Reddy et al. |
| 2018/0169425 | A1 | 6/2018 | Reddy et al. |
| 2018/0193060 | A1 | 7/2018 | Reddy et al. |
| 2018/0214686 | A1 | 8/2018 | De Kock et al. |
| 2018/0296824 | A1 | 10/2018 | De Kock et al. |
| 2018/0344200 | A1 | 12/2018 | Thakur et al. |
| 2018/0344252 | A1 | 12/2018 | An et al. |
| 2019/0054289 | A1 | 2/2019 | Reddy et al. |
| 2019/0054290 | A1 | 2/2019 | De Kock et al. |
| 2019/0117959 | A1 | 4/2019 | Reddy |
| 2019/0151651 | A1 | 5/2019 | Reddy et al. |

OTHER PUBLICATIONS

International Search Report and Wrirren Opinion dated Oct. 29, 2019 for International Application No. PCT/US2019/042995.
Invitation to Pay Additional Fees dated Jul. 26, 2019 for International Application No. PCT/US2019/028506.

* cited by examiner

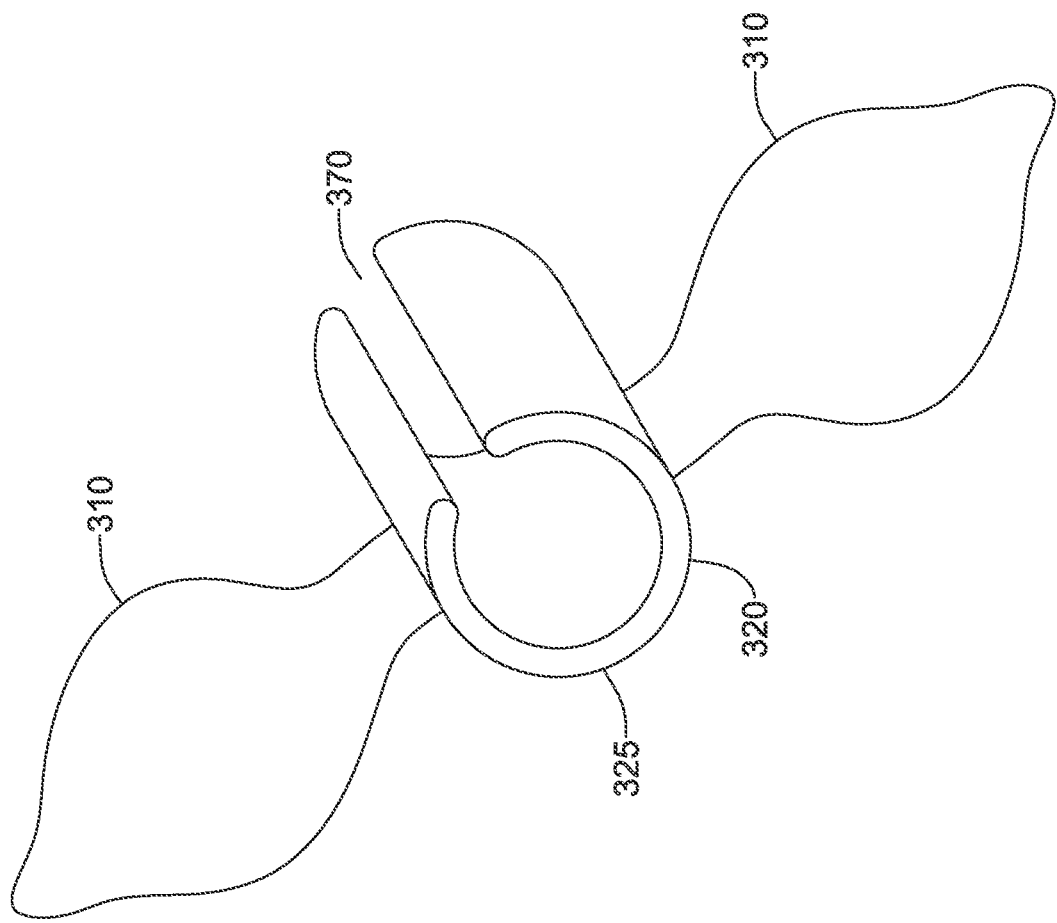

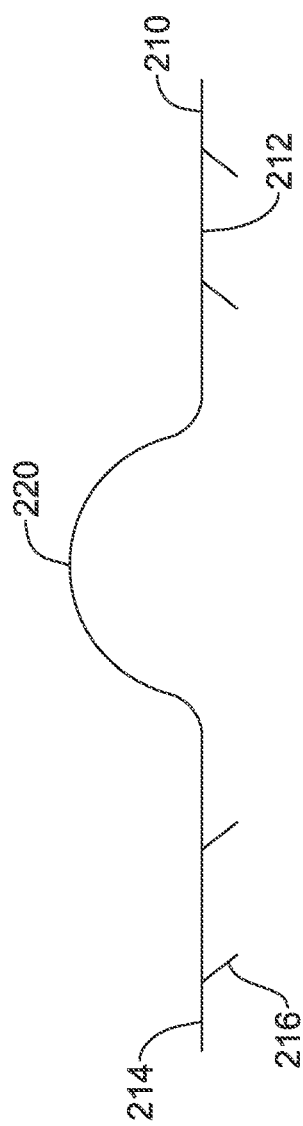

SUBCUTANEOUS LEAD FIXATION MEMBER

CROSS REFERENCE TO RELATED APPLICATIONS

The present application claims the benefit of and priority to U.S. Provisional Patent Application Ser. No. 62/661,589, filed Apr. 23, 2018 and titled SUBCUTANEOUS LEAD FIXATION MEMBER, the disclosure of which is incorporated herein by reference.

BACKGROUND

The implantable defibrillator has been demonstrated to extend patient lives by treatment of potentially deadly arrhythmias. Over time, various efforts have been made to address complications associated with implantation of such devices. The advent of subcutaneous defibrillators with leads implanted beneath the skin and over the ribcage of the patient allows avoidance of past lead failure issues. However, implantation and securement of subcutaneous leads and other medical devices remains a time consuming process with challenges related to the length of the incision required, length of time required for implantation, and manipulation required by physician. This has led to interest in further alternatives for fast, reliable anchoring of subcutaneous leads.

SUMMARY

This disclosure provides design, material, and use alternatives for medical devices, including delivery systems.

A first example includes a retainer clip configured to secure an electrode within a patient's body. The retainer clip includes first and second arms connected by a flexible bridge, the retainer clip configured to move between a first orientation in which lower surfaces of the first and second arms face each other, and a second orientation in which the first and second arms extend laterally from opposite sides of the flexible bridge, wherein the retainer clip is biased in the second orientation.

Alternatively or additionally to the above example, the first and second arms are rigid.

Alternatively or additionally to any of the above examples, the flexible bridge is made of a shape memory material.

Alternatively or additionally to any of the above examples, the flexible bridge extends outward from an upper surface of the first and second arms, transverse to a plane of the first and second arms.

Alternatively or additionally to any of the above examples, the first and second arms have a first width greater than a width of the flexible bridge.

Alternatively or additionally to any of the above examples, first ends of the first and second arms are attached to the flexible bridge and second ends of the first and second arms are tapered to a second width less than the first width.

Alternatively or additionally to any of the above examples, a cross-section taken along a longitudinal axis of the retainer clip extending between second ends of the first and second arms defines at least one curve.

Alternatively or additionally to any of the above examples, the first and second arms have a plurality of protrusions extending outward from the lower surfaces.

Alternatively or additionally to any of the above examples, the protrusions on the first and second arms extend at an angle toward the flexible bridge.

Alternatively or additionally to any of the above examples, the protrusions are formed from curved or V-shaped cuts through the first and second arms and bending a portion of each arm adjacent the cuts downward away from an upper surface of the first and second arms.

Alternatively or additionally to any of the above examples, the flexible bridge is sized and configured to partially surround an electrode.

Alternatively or additionally to any of the above examples, the flexible bridge is C-shaped, the flexible bridge having a back side opposite an opening defining the C, the opening sized and configured to receive an electrode.

Alternatively or additionally to any of the above examples, the first and second arms are attached to the back side of the flexible bridge.

Alternatively or additionally to any of the above examples, the first and second arms are a single monolithic structure attached to the back side of the flexible bridge.

Alternatively or additionally to any of the above examples, the first and second arms are attached to opposite sides of the flexible bridge between the back side and the opening.

Alternatively or additionally to any of the above examples, the first and second arms have a plurality of protrusions extending outward from the lower surfaces.

Alternatively or additionally to any of the above examples, the protrusions on the first and second arms extend at an angle toward the flexible bridge.

Alternatively or additionally to any of the above examples, the protrusions are formed from curved or V-shaped cuts through the first and second arms and bending a portion of each arm adjacent the cuts downward away from an upper surface of the first and second arms.

Another example is a retainer clip and delivery device assembly including a retainer clip including first and second arms connected by a flexible bridge, the retainer clip configured to move between a first orientation in which lower surfaces of the first and second arms face each other, and a second orientation in which the first and second arms extend laterally from opposite sides of the flexible bridge, wherein the retainer clip is biased in the second orientation, and a delivery device including a housing and a plunger, the housing having a lumen configured to receive the retainer clip in the first orientation, the plunger slidingly engaged within the lumen; wherein the retainer clip is delivered by sliding the plunger through the lumen, moving the retainer clip out of the delivery device.

Alternatively or additionally to the above example, the housing and the plunger each have a recess on a bottom surface thereof, positioned such that when the plunger is slid into the housing and the bottom surfaces of the housing and plunger are adjacent each other, the recesses are aligned.

Another example is a method of securing a medical device subcutaneously within a patient. The method includes inserting a medical device into an incision, constraining a retainer clip in a first orientation and inserting the retainer clip into the incision, the retainer clip including first and second arms connected by a flexible bridge, the retainer clip configured to move between the first orientation in which lower surfaces of the first and second arms face each other, and a second orientation in which the first and second arms extend laterally from opposite sides of the flexible bridge, wherein the retainer clip is biased in the second orientation, releasing the retainer clip, thereby allowing the retainer clip to return to the biased second orientation, and securing the retainer clip to the medical device.

Alternatively or additionally to the above example, the incision is 1 cm or less in length and the medical device is a lead.

Alternatively or additionally to any of the above examples, constraining the retainer clip in the first orientation includes squeezing the first and second arms together.

Alternatively or additionally to any of the above examples, securing the retainer clip includes snapping the flexible bridge over the lead.

Alternatively or additionally to any of the above examples, the lead includes one or more groove, and securing the retainer clip includes snapping the flexible bridge into the groove.

Another example is a method of securing a medical device subcutaneously within a patient. The method includes inserting a medical device into an incision, constraining a retainer clip in a first orientation and inserting the retainer clip into a delivery device, the retainer clip including first and second arms connected by a flexible bridge, the retainer clip configured to move between the first orientation in which lower surfaces of the first and second arms face each other, and a second orientation in which the first and second arms extend from opposite sides of the flexible bridge, wherein the retainer clip is biased in the second orientation, wherein the delivery device includes a housing and a plunger, the retainer clip disposed within a lumen in the housing in the first orientation, the plunger slidingly engaged within the lumen, positioning the delivery device over at least a portion of the medical device, sliding the plunger through the lumen, pushing the retainer clip out of the delivery device and into body tissue over the portion of the medical device, wherein the retainer clip returns to the biased second orientation upon release from the delivery device and secures the retainer clip to the medical device.

Another example is a method of subcutaneously implanting a device in a patient, including making an incision in skin of a patient, inserting a device into the incision in contact with deep fascia and below adipose tissue, leaving at least a portion of the device exposed at the incision, inserting a fixation member in a first configuration into the incision and over at least a portion of the device, the fixation member having first and second arms connected by a bridge, wherein at least the bridge is flexible, the first configuration having lower surfaces of the first and second arms facing each other, moving the fixation member to a second configuration wherein at least a middle portion of the fixation member is in contact with the device, and securing the fixation member to the deep fascia, thereby fixing the device within the patient.

Alternatively or additionally to the above example, the device is a lead for a subcutaneous cardiac defibrillator and the bridge of the fixation member has a semi-circular shape in both the first and second configurations, sized to match a shape of the lead.

Alternatively or additionally to any of the above examples, the incision is a xiphoid incision of 1 cm or less.

Alternatively or additionally to any of the above examples, the method further comprises, after inserting the lead into the xiphoid incision, advancing the lead subcutaneously to a location of an implanted defibrillator.

Alternatively or additionally to any of the above examples, the first and second arms of the fixation member are rigid such that in the first configuration the first and second arms are substantially parallel and in the second configuration the first and second arms are substantially planar.

Alternatively or additionally to any of the above examples, the first and second arms each have a central width larger than a width of the bridge.

Alternatively or additionally to any of the above examples, the first and second arms taper from the central width to an end width that is smaller than the central width.

Alternatively or additionally to any of the above examples, a side profile of the first and second arms is curved.

Another example is a coil and delivery device assembly for securing an electrode lead within a patient's body. The device assembly comprises a coil configured to move between a first, linear orientation and a second helical coil orientation, wherein the coil is biased in the second helical coil orientation, and a delivery device including a housing and an actuator, the housing having a channel configured to receive the coil in the first, linear orientation, the actuator disposed within the channel and configured to move the coil through the channel and out of the housing, the housing having a recess in a bottom end thereof, configured to at least partially receive an electrode lead and position the coil for deployment around the electrode lead as the coil is moved through the channel and out of the delivery device.

Alternatively or additionally to the above example, the actuator includes a tab extending out a top end of the channel and a plunger extending into the channel.

Alternatively or additionally to any of the above examples, the bottom end of the housing includes an extension including the channel, the extension extending below the bottom end of the housing.

Alternatively or additionally to any of the above examples, the coil includes a shape set section of a wire and a straight section of wire connected to the shape set section by a breakaway notch, wherein the shape set section, when separated at the breakaway notch and delivered out of the housing, returns to the second helical coil orientation.

Alternatively or additionally to any of the above examples, the actuator is attached to the straight section of wire, the actuator configured to rotate, thereby breaking the breakaway notch and separating the straight section of wire from the shape set section after the shape set section has been deployed into the second helical coil orientation.

Alternatively or additionally to any of the above examples, the coil includes two or more shape set sections connected by breakaway notches.

Alternatively or additionally to any of the above examples, the housing includes a lumen extending at least part way therethrough, the lumen configured to receive the coil after it is delivered out the bottom end of the channel and curves around the electrode lead.

Alternatively or additionally to any of the above examples, the lumen is configured to receive multiple turns of the coil.

Another example is a method of subcutaneously implanting a medical device in a patient. The method comprises inserting a medical device into an incision to a subcutaneous position, inserting a delivery device into the incision, the delivery device including a housing and an actuator, the housing having a channel containing a coil in a first, linear orientation, the actuator disposed within the channel and configured to move the coil through the channel and out of a bottom surface of the housing where the coil will move to a second helical coil orientation, the housing having a recess in a bottom end thereof configured to at least partially receive the medical device and position the coil for deployment around the medical device, positioning the housing with the recess disposed over the medical device, and moving the actuator thereby moving the coil out of the bottom surface of the housing, wherein the coil penetrates tissue under the medical device and curves around the medical device as the coil moves into the second helical coil orientation, thereby securing the medical device to tissue within the incision.

Alternatively or additionally to the above example, before inserting the medical device, the method further includes making an incision of less than 1 cm.

Alternatively or additionally to any of the above examples, the bottom end of the housing includes an extension including the channel, the extension extending below the bottom end of the housing, where positioning the housing includes contacting the medical device with the recess of the housing, thereby holding the medical device against tissue with the extension also in contact with the tissue.

Alternatively or additionally to any of the above examples, the coil includes a shape set section of a wire and a straight section of wire connected to the shape set section by a breakaway notch, the shape set section defining the coil, the actuator connected to the straight section of wire, wherein moving the actuator includes moving the straight section of wire through the channel to push the shape set section out of the housing, through tissue and around the medical device as the shape set section of wire returns to the biased helical coil orientation, the method further comprising rotating the actuator to break the breakaway notch, thereby separating the coil from the straight section of wire.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 6C is a perspective view of another exemplary retainer clip;

FIGS. 8A and 8B are top and side views, respectively, of another exemplary retainer clip;

DETAILED DESCRIPTION

Figure 1:
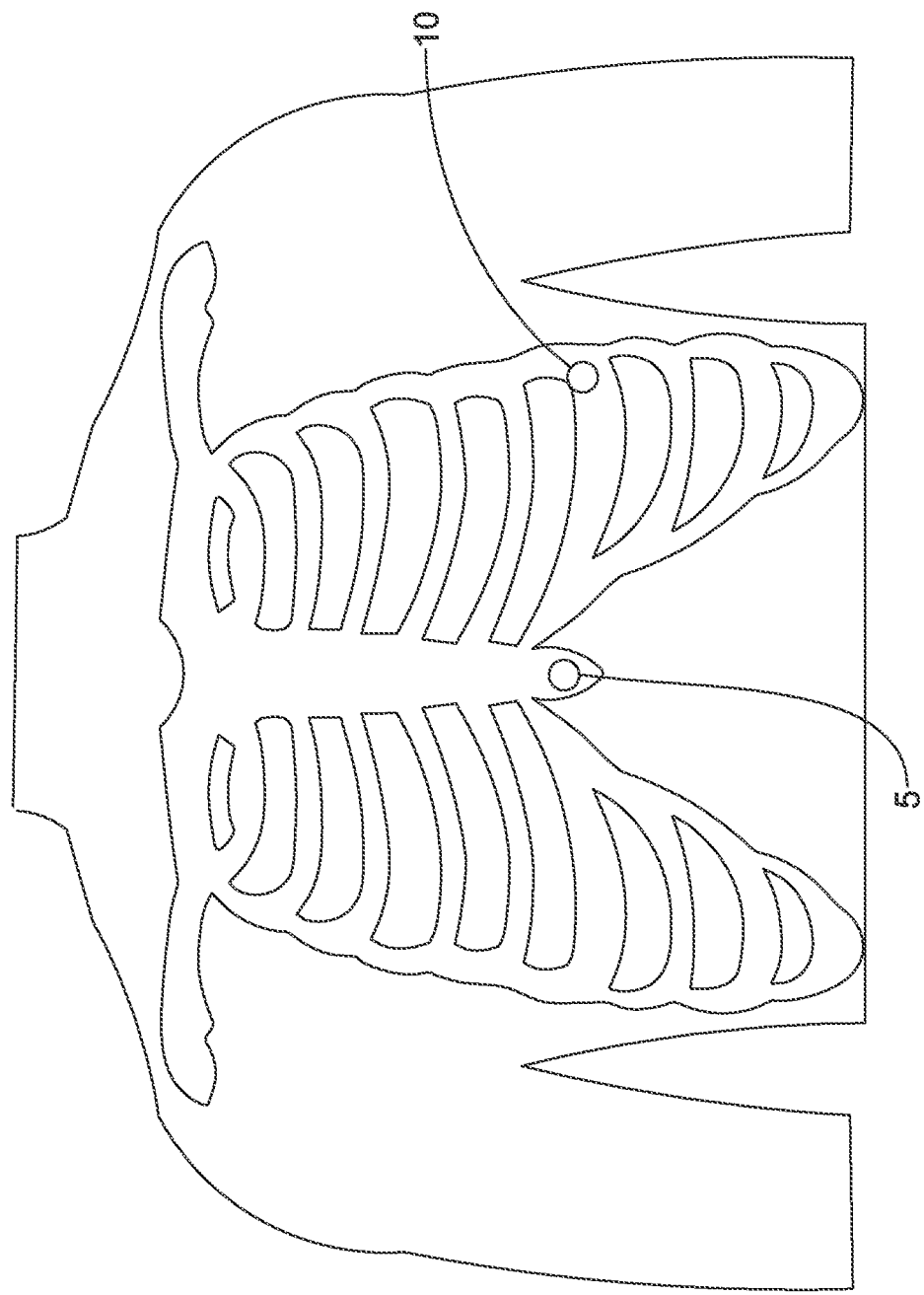
FIG. 1 is an illustration of incision placement for subcutaneous implantation of a medical device.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5). Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "withdraw", variants thereof, and the like, may be generally considered with respect to the positioning, direction, and/or operation of various elements relative to a user/operator/manipulator of the device, wherein "proximal" and "withdraw" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The following description should be read with reference to the drawings, which are not necessarily to scale, wherein similar elements in different drawings are numbered the same. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

The subcutaneous implantable cardioverter defibrillator (S-ICD) system from Boston Scientific provides benefits to the patient including the preservation of transvenous anatomy and avoidance of intracardiac leads, which may fracture and/or may serve as conduits for infection to reach the heart, and can occlude blood vessels going into the heart, making later placement of leads or other devices in the heart more difficult. An example and discussion of subcutaneous lead implantation may be found in US Publication No. 20120029335, titled SUBCUTANEOUS LEADS AND METHODS OF IMPLANT AND EXPLANT, the disclosure of which is incorporated herein by reference.

In some examples, small, permanently implantable fixation members may be used in conjunction with subcutaneous implantable medical devices. The medical device may be a subcutaneous lead, electrode, implantable loop recorder, implantable microchip, or other device benefiting from a securing element to permanently implant the device subcutaneously in the body. In some examples, the medical device may be a S-ICD lead.

FIG. 1 illustrates two incisions that may be involved with placement of an implantable S-ICD lead. A minimal xiphoid incision 5 may be made for the permanent implantation of a medical device. The xiphoid incision may be less than 1 cm long, though it may be larger if desired. A lead may be tunneled beneath the skin to a device pocket 10. A small portion of the lead may remain exposed at the xiphoid incision 5, and a fixation member may be used to secure the lead to the xiphoid process or sternum. A medical device, such as an implantable pulse generator, may be implanted at the device pocket 10. In the example, shown, the device pocket 10 is located at about the left axilla, such as between the anterior axillary line and the posterior axillary line, or at about the midaxillary line. This specific position is shown for illustrative purposes; the present invention may be used for implanting devices at other subcutaneous positions, such as near the spine, or higher on the chest such a near the clavicle or over the $1^{st}$ or $2^{nd}$ ribs.

Figure 2A:
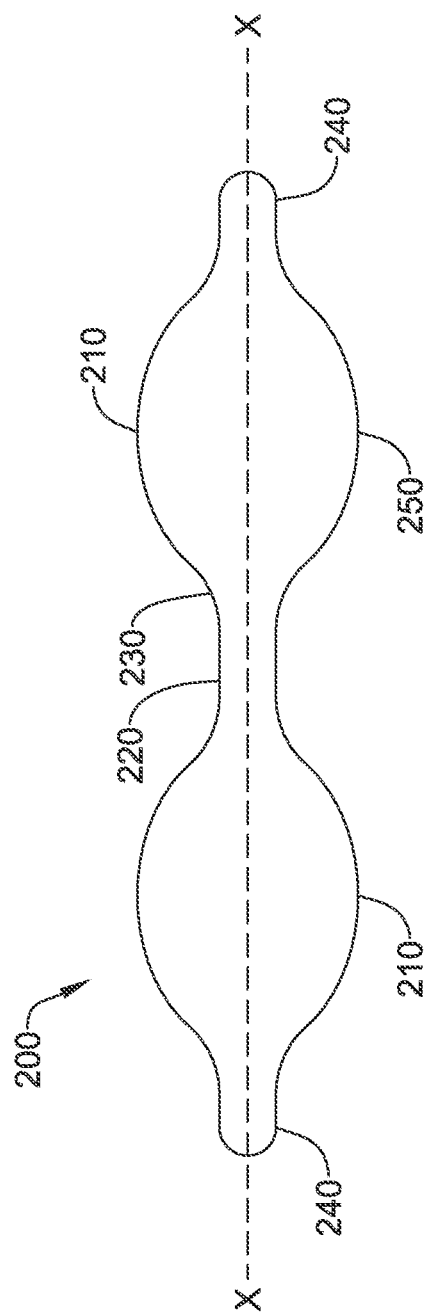
FIG. 2A is a top view of an exemplary retainer clip.
Figure 2B:
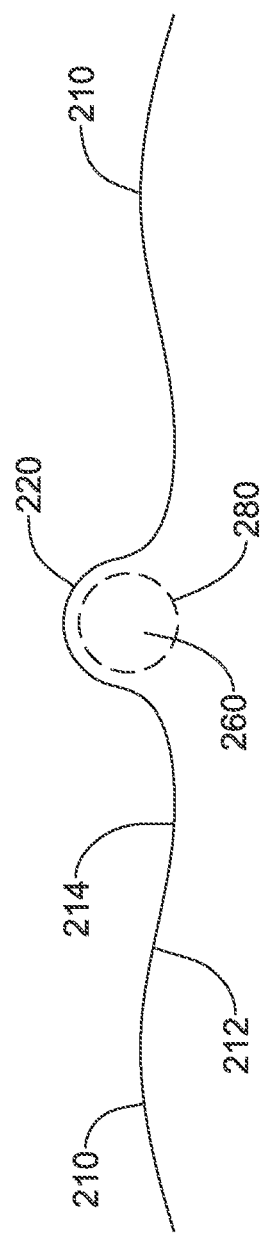
FIGS. 2B and 2C are side views of the retainer clip of FIG. 2A in different orientations.
Figure 2C:
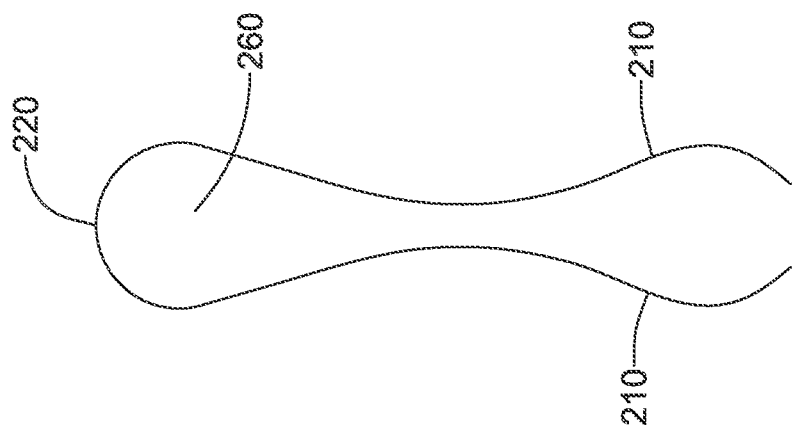

FIGS. 2A-2C illustrate an exemplary fixation member in the form of a retainer clip 200. The retainer clip 200 may have first and second arms 210 connected by a bridge 220. The first and second arms 210 may be symmetric, that is, each having the same size and shape, as illustrated in FIGS. 2A-2C, or they may have different shapes and sizes. The arms 210 may have first ends 230 attached to the bridge 220. The bridge 220 may be flexible, allowing the retainer clip 200 to move between a first, constrained orientation in which lower surfaces 212 of the first and second arms 210 face each other, as shown in FIG. 2C, and a second orientation in which the first and second arms 210 extend substantially laterally from opposite sides of the bridge 220, as shown in FIGS. 2A and 2B. The retainer clip 200 may be biased in the second orientation.

In some examples, as shown in FIG. 2A, the arms 210 may have a width in a central region that is greater than the width of the bridge 220. The arms 210 may taper from the central region 250 to the first ends 230 and from the central region 250 to the second ends 240. Tapered, atraumatic second ends 240 may facilitate the arms digging into tissue, such as fascial tissue, to secure the retainer clip 200 at a desired position.

The larger center width of arms 210 may prevent the retainer clip 200 from migrating. In some examples, the arms 210 may be rigid, maintaining a constant shape as the retainer clip 200 moves between the first and second orientations. In other examples, at least a portion of the arms 210 may be flexible. For example, the first ends 230 of the arms 210 may be flexible, providing increased flexibility to the retainer clip 200 for moving between the first and second orientations. Alternatively, the bridge 220 may be rigid, and the first ends 230 of the arms 210 may be flexible to provide the movement between the first and second orientations of the retainer clip 200.

In some examples, the bridge 220 may be made of a shape memory material, including metal and polymer shape memory materials. In other examples, the bridge 220 may be formed by one or more nitinol wires and the arms 210 may be formed by overmolding plastic paddles onto the nitinol wires, such that the bridge 220 is flexible while the arms 210 are rigid. A silicon layer may be disposed over the upper surface 214 of the arms 210 and/or the bridge 220. Other materials may be used as desired.

Figure 7:
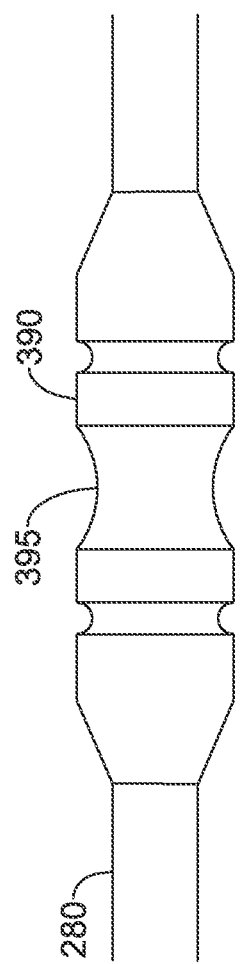
FIG. 7 is a top view of an exemplary mating element on an electrode lead.

The bridge 220 may extend outward from the upper surface 214 of the arms 210, transverse to the plane of the arms 210, as shown in FIG. 2B. The extension may create a recess 260 sized and shaped to receive at least a portion of the medical device to be secured. In the example shown in FIG. 2B, the recess 260 is sized and shaped to receive and at least partially surround a subcutaneous lead 280, shown in dashed lines. Also as seen in FIG. 2B, when viewed in cross section taken along a longitudinal axis X-X of the retainer clip 200, the first and second arms 210 of the retainer clip 200 may each define at least one curve. In some examples, rather than be adapted to secure to the lead itself, as shown, the retainer clip 200 may be adapted to secure to a sleeve placed on or over a lead, or built into the lead, such as, for example, a device as shown in FIG. 7, below.

The flexibility of the retainer clip 200 allows for insertion into a small incision. The retainer clip 200 is folded into the first orientation, as shown in FIG. 2C, and then inserted into the incision over the device to be secured.

Figure 3:
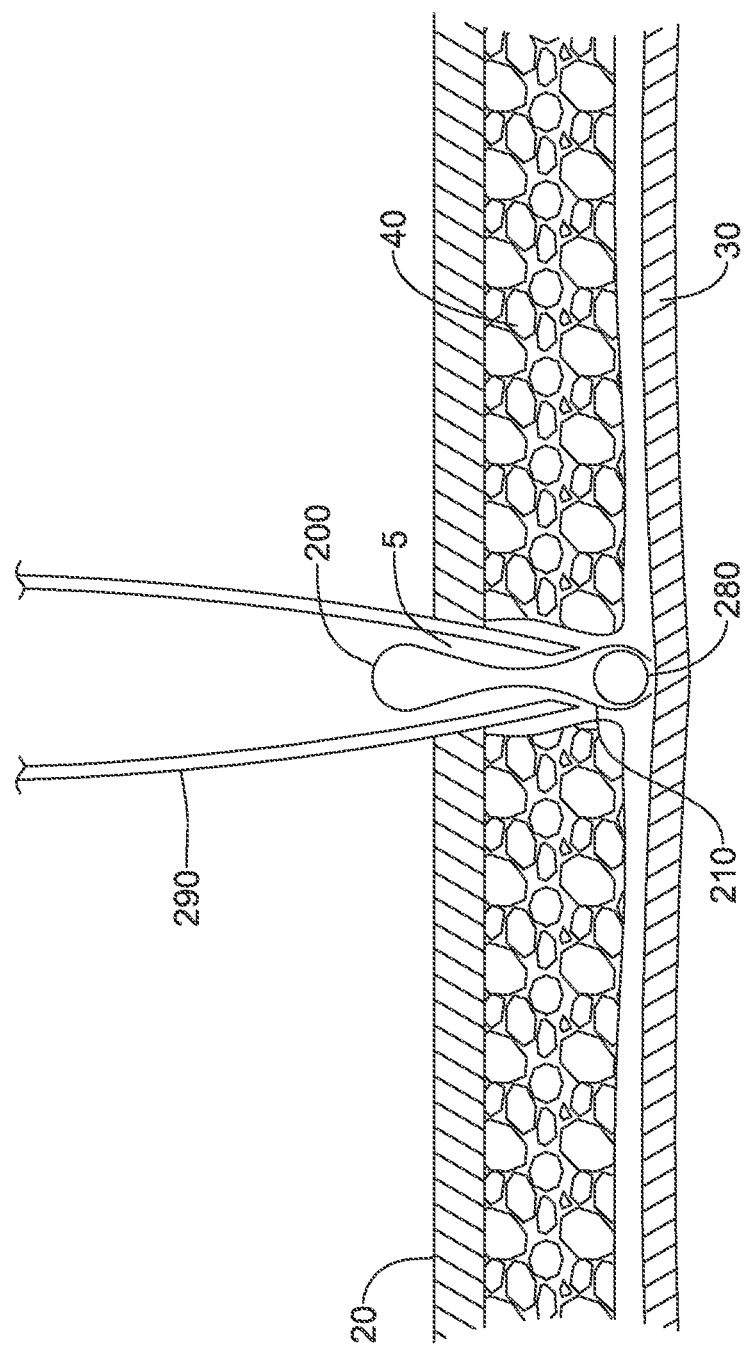
FIG. 3 is a cross-sectional illustration of the retainer clip of FIGS. 2A-2C being implanted subcutaneously.
Figure 4:
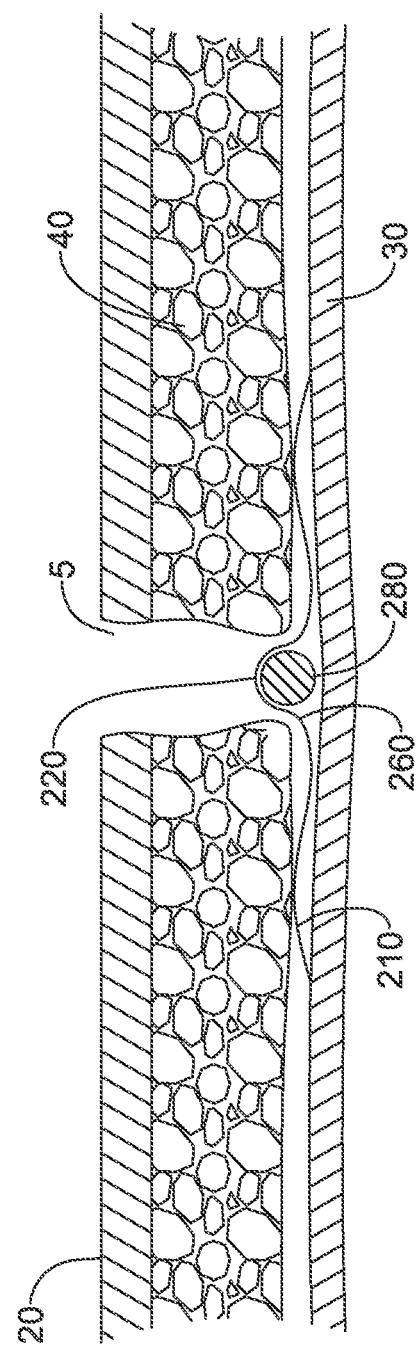
FIG. 4 is a cross-sectional illustration of the retainer clip of FIGS. 2A-2C after subcutaneous implantation.
Figure 5:
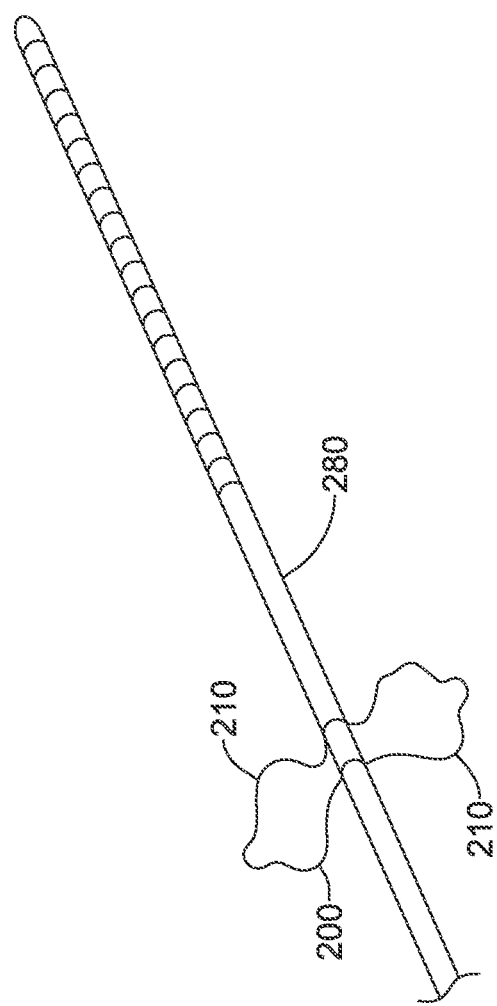
FIG. 5 is a perspective view the retainer clip of FIGS. 2A-2C disposed on an electrode lead.

FIGS. 3-5 illustrate subcutaneous implantation of an S-ICD lead 280 using a clip as illustrated. The lead 280 was previously inserted into an incision 5 and tunneled under the skin 20. The lead 280 may be placed under the skin 20 and fatty tissue 40, above the fascial plane 30. As shown in FIG. 3, a tool such as forceps 290 may be used to hold the arms 210 of the retainer clip 200 together. The retainer clip 200 may be inserted into the incision 5 and over the lead 280 in the first orientation. Releasing the arms 210 allows the retainer clip 200 to automatically move back into the relaxed, second orientation. The recess 260 in the bridge 220 fits over the lead 280, and the relatively thin arms 210 slide between the fatty tissue 40 and the fascial plane 30, thereby securing the lead 280 in place, as shown in FIG. 4. The retainer clip 200 may prevent the lead 280 from migrating away from the implantation site. FIG. 5 illustrates a retainer clip 200 in place over a lead 280. The structure of the retainer clip 200 allows it to be placed over the lead 280 with the first and second arms 210 extending transverse to the longitudinal axis of the lead 280. Rather than a forceps 290 as shown in FIGS. 3-5, the retainer clip 200 could also be placed using a specialized tool such as a combination bore and plunger as illustrated below in FIGS. 9A-9C.

Figure 6A:
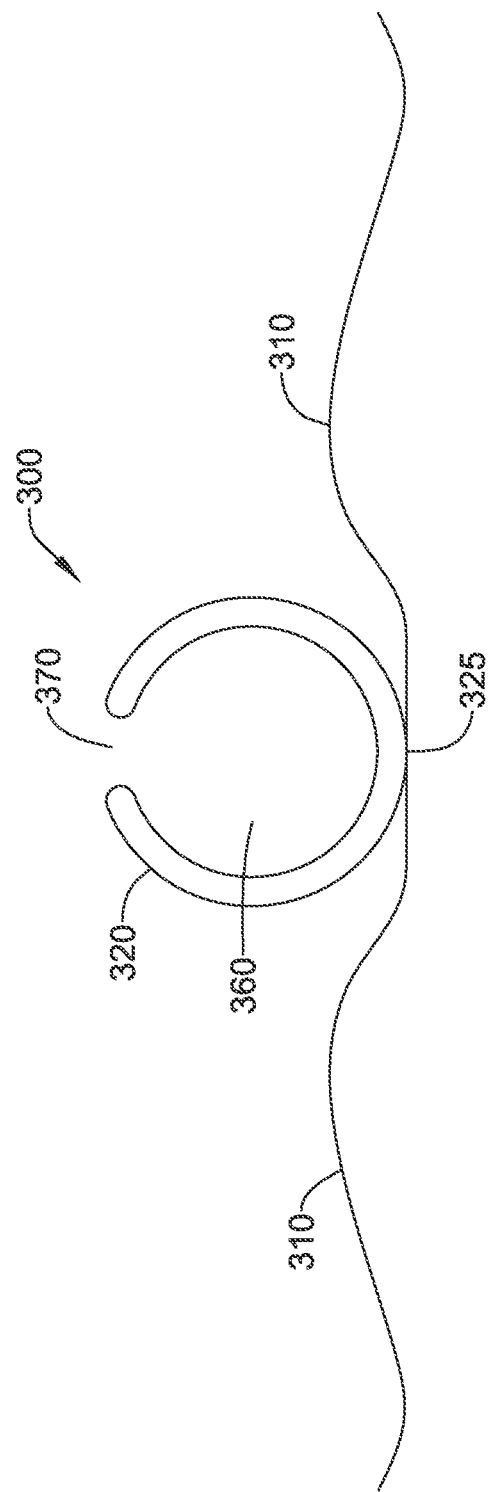
FIG. 6A is a side view of another exemplary retainer clip.
Figure 6B:
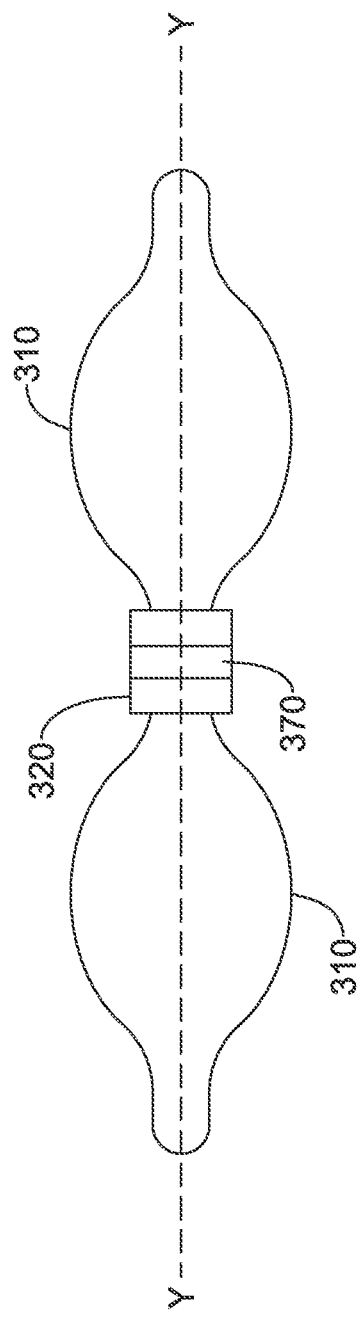
FIG. 6B is a top view of the retainer clip of FIG. 6A.

FIGS. 6A-6C illustrate another example retainer clip 300. The retainer clip 300 may be similar to the retainer clip 200 shown in FIGS. 2A-2C, but with a C-shaped bridge 320. First and second arms 310 may be separate elements connected to the back side 325 of the bridge 320, opposite the opening 370 defining the C. In other examples, the separate first and second arms 310 may be attached to opposite sides of the bridge 320, between the back side 325 and the opening 370, as shown in FIG. 6C. Alternatively, the first and second arms 310 may be defined by a single monolithic piece, with a middle portion attached to the back side 325 of the bridge 320. At least a portion of the bridge 320 may be flexible, allowing the opening 370 to expand to snap over a cylindrical medical device within the recess 360 defined by the C-shaped bridge 320. The opening 370 may extend transverse to the longitudinal axis Y-Y of the retainer clip 300, as shown in FIG. 6B. The bridge 320 may be sized for snapping onto and securing a lead in the recess 360 or, alternatively, it may be designed to work with a device as in FIG. 7.

The lead 280 may include one or more features configured to mate with the retainer clip 200, 300. FIG. 7 shows an example lead 280 with a mating element 390 including a notch 395 for receiving the bridge 220, 320 of the retainer clip 200, 300. The mating element 390, and the notch 395 in particular, may prevent axial movement of the lead 280 within the retainer clip 200, 300. The mating element 390 may further dictate placement of the retainer clip 200, 300 at a specified location relative to sensing and/or shocking electrodes. The mating element 390 may be a structure permanently affixed to the lead 280. In other examples, the mating element 390 may be added to the lead, similar to a conventional suture sleeve.

In some examples, the retainer clip 200, 300 may be permanently fixed onto the lead 280. Either a removable or permanently fixed retainer clip 200, 300 may serve as an active electrode for sensing electrical signals and/or may offer pacing signals. In a removable retainer clip 200, 300, the electrode may contain an electrode surface that an electrically conductive portion of the retainer clip 200, 300 clamps over allowing a connection to facilitate electrical signals. For example, the notch 395 in the mating element 390 may include an electrode surface that contacts an electrode surface on the inner surface of the bridge 220, 320, providing the electrical connection.

Figure 8A:
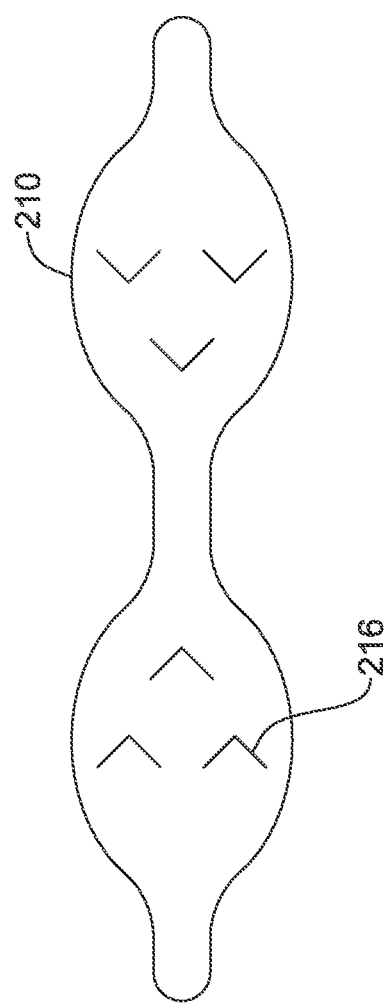

The clip retainer 200 may include one or more protrusions 216 extending outward from the lower surface 212 of the first and second arms 210, as shown in FIGS. 8A, 8B. While the retainer clip 200 is illustrated in FIGS. 8A, 8B, it will be understood that the protrusions 216 may be provided on the retainer clip 300 as well. The protrusions 216 may extend at an angle toward the bridge 220, with the protrusions 216 on each arm 210 extending in opposite directions, as shown in FIG. 8B. The protrusions 216 may be formed from curved or V-shaped cuts through the first and second arms 210 followed by bending a portion of the arm 210 adjacent the cuts downward away from the upper surface 214 of the first and second arms 210. The protrusions 216 may provide enhanced fixation into the fascial plane.

Figure 9A:
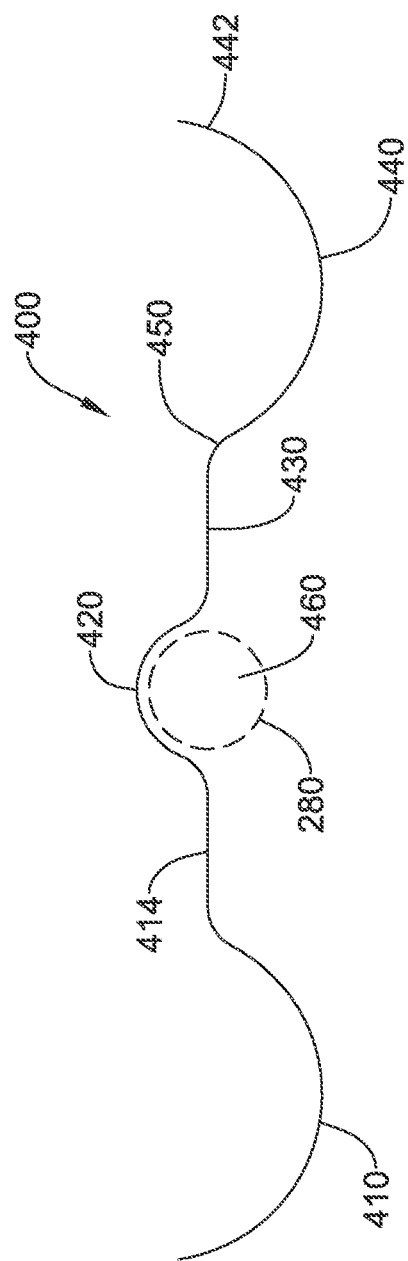
FIG. 9A is a side view of an exemplary staple in a second, relaxed orientation.
Figure 9B:
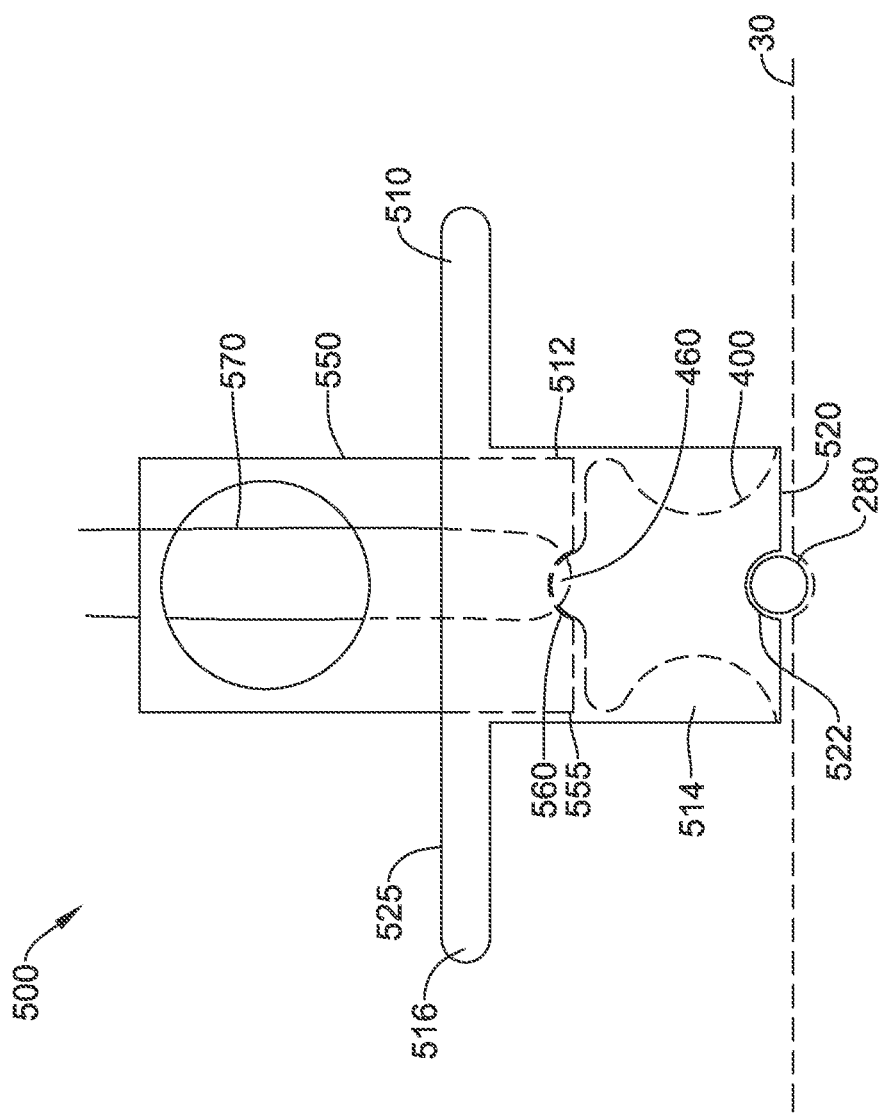
FIG. 9B is a side view of an exemplary insertion device with the staple of FIG. 9A loaded in the first orientation.

An alternate fixation member and insertion device is shown in FIGS. 9A and 9B. The fixation member may be a staple 400 configured to move between a first, compressed configuration shown in FIG. 9B to a second, relaxed configuration, shown in FIGS. 9A and 9C. The staple 400 may be loaded into the insertion device 500 in the first configuration, as shown in FIG. 9B, and when the staple 400 is delivered out of the insertion device 500, the staple may move automatically into the second, relaxed configuration, shown in FIG. 9A. The insertion device 500 may include a housing 510 and plunger 550. The housing 510 may have a lumen 512 extending therethrough, with a cavity 514 located adjacent the first end 520 of the housing 510. The lower end 520 of the housing 510 may have a recess 522 sized and configured to receive the lead 280. The cavity 514 may be sized and configured to receive the staple 400 in the first configuration. The upper end 525 of the housing 510 may have a laterally extending protrusion or flange 516. The plunger 550 may be sized to slide into the lumen 512 and push the staple 400 out the lower end 520 of the housing 510. The lower end 555 of the plunger 550 may include a recess 560 shaped and configured to match the protruding bridge 420. The recess 560 may allow the plunger 550 to push the staple 400 out of the housing 510 without deforming the bridge 420.

Figure 9C:
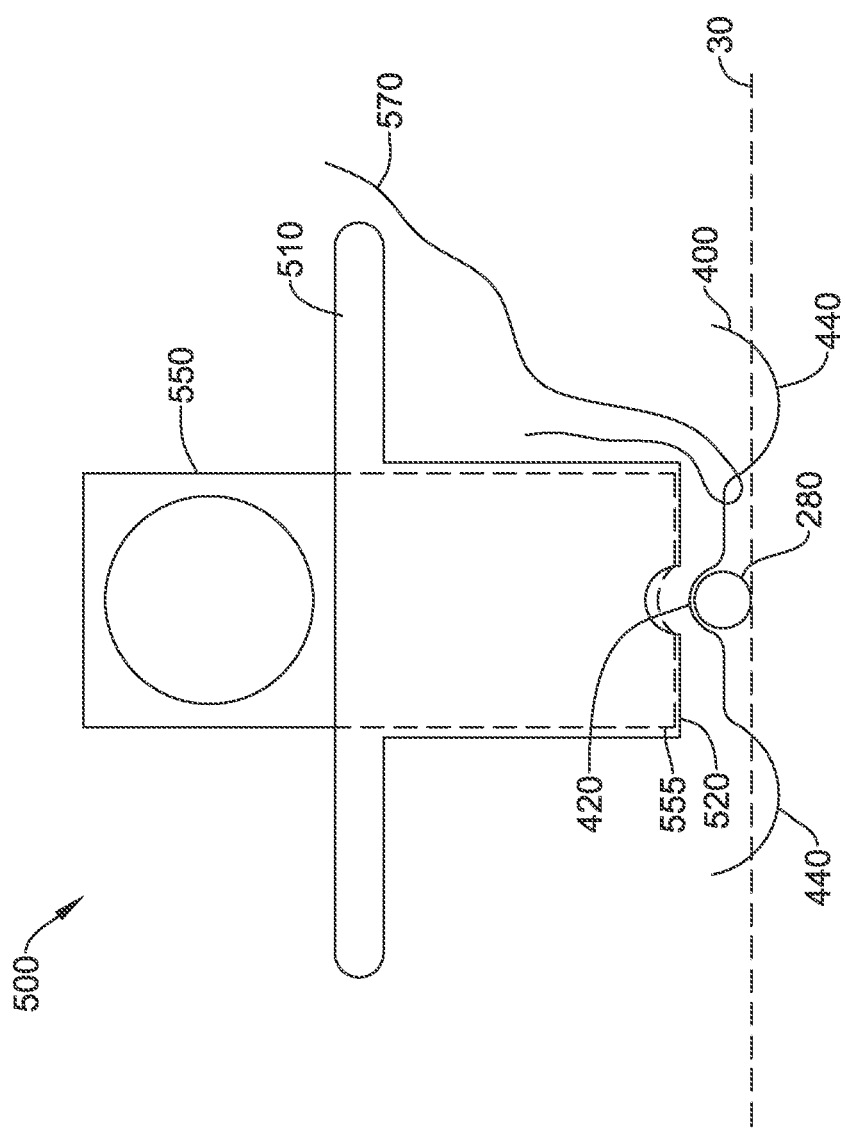
FIG. 9C is a side view of the insertion device of FIG. 9B in the deployed configuration showing the staple implanted over a lead.

The staple 400 may be a single elongate monolithic element. In some examples, the staple 400 may be a wire that is round, flat, or any other shape. The staple 400 may define first and second arms 410 separated by a bridge 420. The arms 410 may each have an inner region 430 and an outer region 440 joined by a flexible region 450. In some examples, the inner region 430 and the outer region 440 may define curves extending in opposite directions, as shown in FIG. 9A. The flexible region 450 of each arm 410 may allow the staple 400 to move between the first orientation in which the outer regions 440 of the first and second arms 410 face each other, as shown in FIG. 9B, and the second orientation in which the first and second arms 410 extend outward from opposite sides of the bridge 420, as shown in FIGS. 9A and 9C. The staple 400 may be biased in the second orientation.

The bridge 420 may protrude upward from the upper surface 414 of the inner region 430 of the arms 410, creating a recess 460 sized and shaped to receive at least a portion of the medical device to be secured. In the example shown in FIGS. 9A and 9C, the recess 460 is sized and shaped to receive and at least partially surround a subcutaneous lead 280, shown in dashed lines. As seen in FIGS. 9A and 9C, the side view of the staple 400 shows the first and second arms 410 defining at least two curves. The bridge 420 may be flexible or rigid, configured to snap onto the lead 280. In some examples, the bridge 420 may be made of a shape memory material, including metal and polymer shape memory materials.

The insertion device 500 may also include a retraction thread 570. The plunger 550 may have a lumen extending therethrough. The retraction thread 570 may extend through the lumen of the plunger 550, around the staple 400 and out the plunger, as shown in FIG. 9B. The retraction thread 570 allows the staple 400 to be removed and/or repositioned. After implantation of the staple 400, if the position is as desired, the retraction thread 570 may be removed by pulling one end of the thread 570, as shown in FIG. 9C.

In use, a staple 400 may be loaded into the insertion device 500 in the first orientation, positioned in the cavity 514 as shown in FIG. 9B. After the lead 280 is implanted through an incision, the insertion device 500 may then be placed into the incision with the recess 522 in the lower end 520 of the housing 510 placed over the lead 280. The plunger 550 may then be depressed, using the flange 516 as leverage. As the plunger 550 is depressed, the staple 400 is pushed out the first end 520 of the housing 510. As the staple exits the housing 510, the ends 442 of the staple 400 penetrate the fascial plane 30. In some examples, the ends 442 may be pointed or sharpened to facilitate penetration of the staple into tissue. The outer regions 440 of each arm are curved, allowing the ends 442 to curve into and then out of the fascial plane 30 as the staple 400 is fully released from the insertion device 500 and returns to the second orientation. As shown in FIG. 9C, the bridge 420 of the staple 400 fits over the lead 280 and holds the lead 280 against the fascial plane 30. The outer regions 440 of the staple 400 extend into and then out of the fascial plane 30, thereby securing the lead 280 to the fascial plane 30. The staple 400 may extend partially or fully through the fascial plane 30. If the staple 400 position is acceptable, the retraction thread 570 is then removed by pulling on one end of the retraction thread 570, as shown in FIG. 9C.

If the staple 400 needs to be repositioned or removed, the user may pull on both ends of the retraction thread 570 at the same time to remove the staple 400. The staple 400 may be redeployed by re-inserting the staple 400 into the cavity 514 of the housing 510 and then redeploying the staple 400 as discussed above.

The staple 400 may be made of a shape memory metal, such as nitinol. In other examples, the staple 400 may be made of a shape memory polymer. The staple 400 allows for securing leads and other medical devices without the use of a suture. A staple 400 may be preloaded into the insertion device 500 providing advantages of being fast and easy to use, greatly reducing the procedure time as compared to securing a lead using sutures. The staple 400 secures the lead 280 to the fascia in a similar manner and location compared to conventional sutures, but has a lower profile than the suture sleeves conventionally used with sutures. The insertion device 500 may be used in smaller incisions as compared to those needed for manipulation of sutures. The incision may be 1 cm or less. The staple 400 and insertion device 500 also provide the advantage of allowing the staple 400 to be repositioned and redeployed easily.

The insertion device 500 may also be used with the retainer clip 200, 300 shown in FIGS. 2A-2C and 6A-6C. The retainer clip 200, 300 may be loaded into the cavity 514 in the compressed orientation as shown in FIG. 3.

Figure 10A:
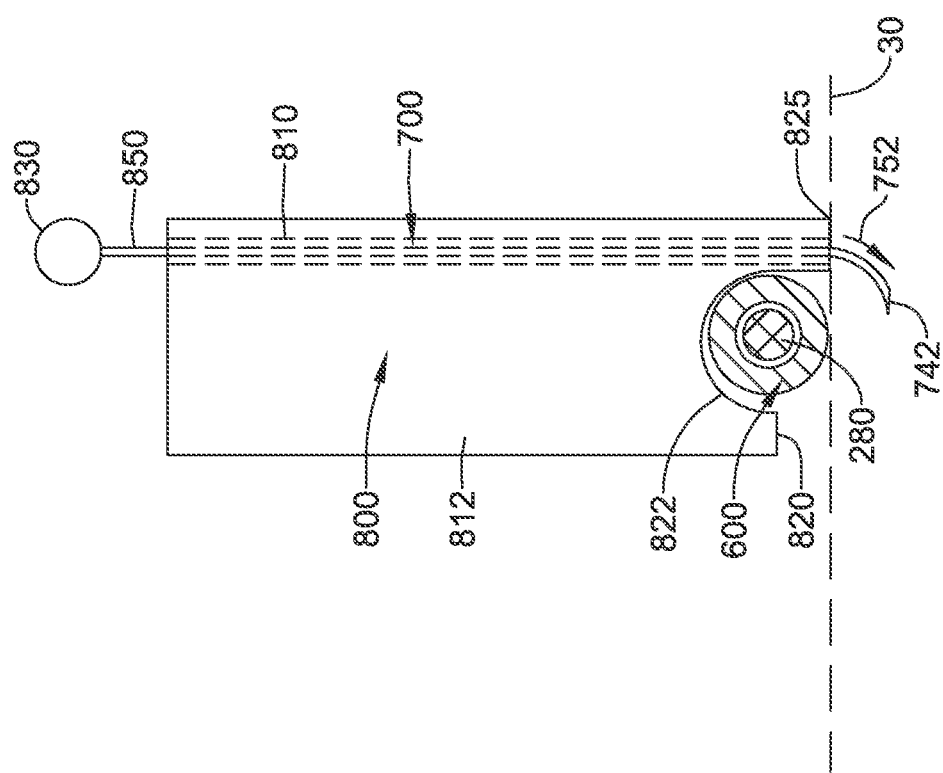
FIG. 10A is a side view of another exemplary insertion device with a helical coil partially deployed around a lead.

Another example fixation member and insertion device are shown in FIGS. 10A-13. The fixation member may be a helical coil 700 configured to move between a first, straight configuration while in the deployment device 800, shown in FIG. 10A, to a second, relaxed configuration upon implantation, shown in FIGS. 12 and 13. The coil 700 may be loaded into the deployment device 800 in the first configuration, as shown in FIG. 10A, and when the coil 700 is delivered out of the deployment device 800, the coil 700 may move automatically into the second, relaxed configuration, shown in FIGS. 12-13.

The deployment device 800 may be tubular in shape and have a lumen 812 extending at least part way therethrough, with a lower end 820 having a recess 822 sized and configured to receive the lead 280. In some examples, a suture sleeve 600 may be disposed around the lead 280, with the recess 822 sized to receive the suture sleeve 600, as shown in FIG. 10A. The deployment device 800 may have a channel 810 extending along one edge that is sized and configured to receive the helical coil 700 in the first, straight configuration. The deployment device 800 may have an actuator 830 connected to a wire 710 extending into the upper end of the channel 810. The deployment device 800 may have an extension 825 including the channel 810, extending below the level of the lower end 820. The extension 825 includes a lower opening of the channel 810. When the recess 822 in the lower end 820 of the deployment device 800 is in position over a lead 280 and suture sleeve 600, the extension 825 may be in contact with the fascial plane 30, allowing the coil 700 to exit the deployment device 800 directly into the fascial plane 30, as shown in FIG. 10A.

Figure 12:
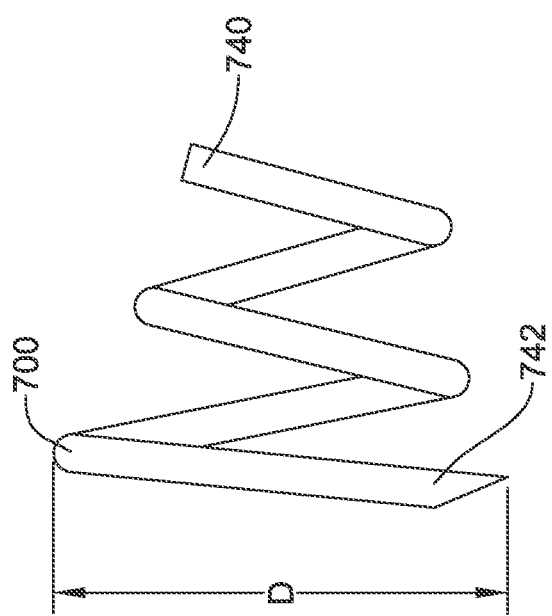
FIG. 12 is a top view of the helical coil of FIGS. 10A-11 in a relaxed state.
Figure 13:
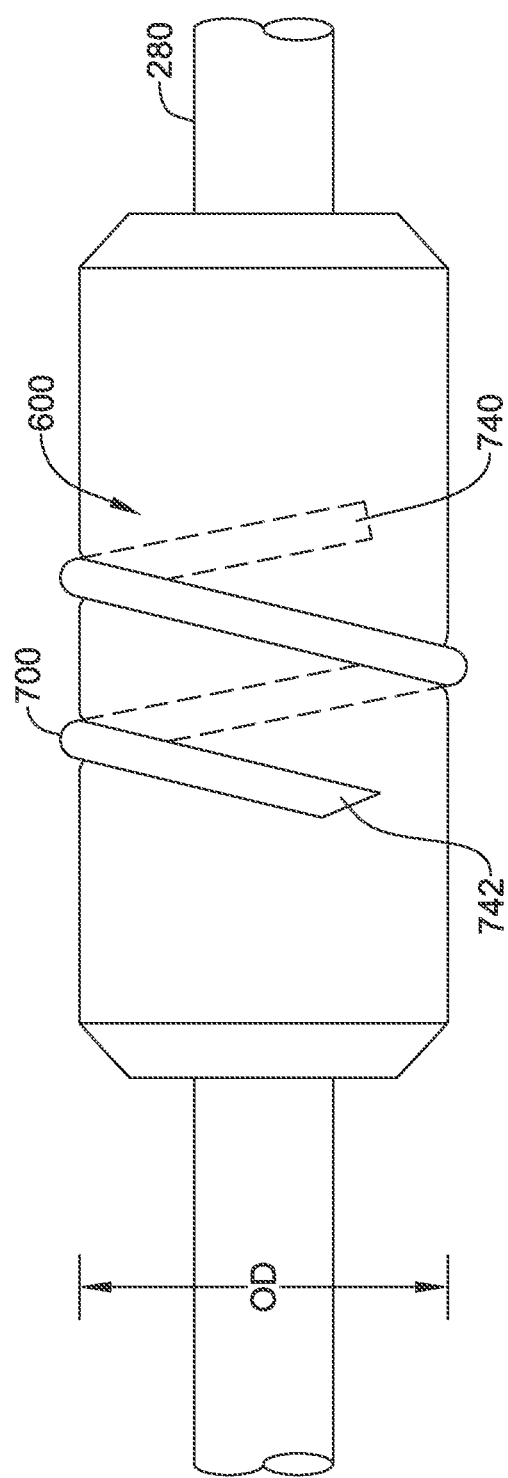
FIG. 13 is a top view of the helical coil of FIG. 12 deployed over a lead.

The coil 700 may be a single elongate monolithic element. In some examples, the coil 700 may be a wire that is round, flat, or any other shape. The coil 700 may be configured to move between the first, linear orientation when constrained within the channel 810 in the deployment device 800, and a second, relaxed helical orientation, as shown in FIGS. 12-13. The coil 700 may be biased in the second orientation.

The coil 700 may be loaded into the channel 810 in the deployment device 800 with one end 742 of the coil positioned within the extension 825. An actuator 830 may be inserted into the upper end of the channel, into contact with the coil 700. The actuator 830 may be in the form of a tab disposed on the end of a plunger 850 that fits into the channel 810. After the lead 280 with an attached suture sleeve 600 is implanted through an incision, the deployment device 800 may then be placed into the incision with the recess 822 placed over the suture sleeve 600 on the lead 280. The actuator 830 may be depressed to move the coil 700 out of the bottom end of the channel 810. The coil 700 curves as it transitions into the relaxed, helical second orientation. The coil 700 may move in the direction of arrow 752 as shown in FIG. 10A. As the coil 700 continues to advance out of the channel 810, the coil 700 curves through the fascial plane 30 and around the suture sleeve 600 and back into the deployment device lumen 812 through the lower end 820, as shown in FIG. 10B.

Figure 10B:
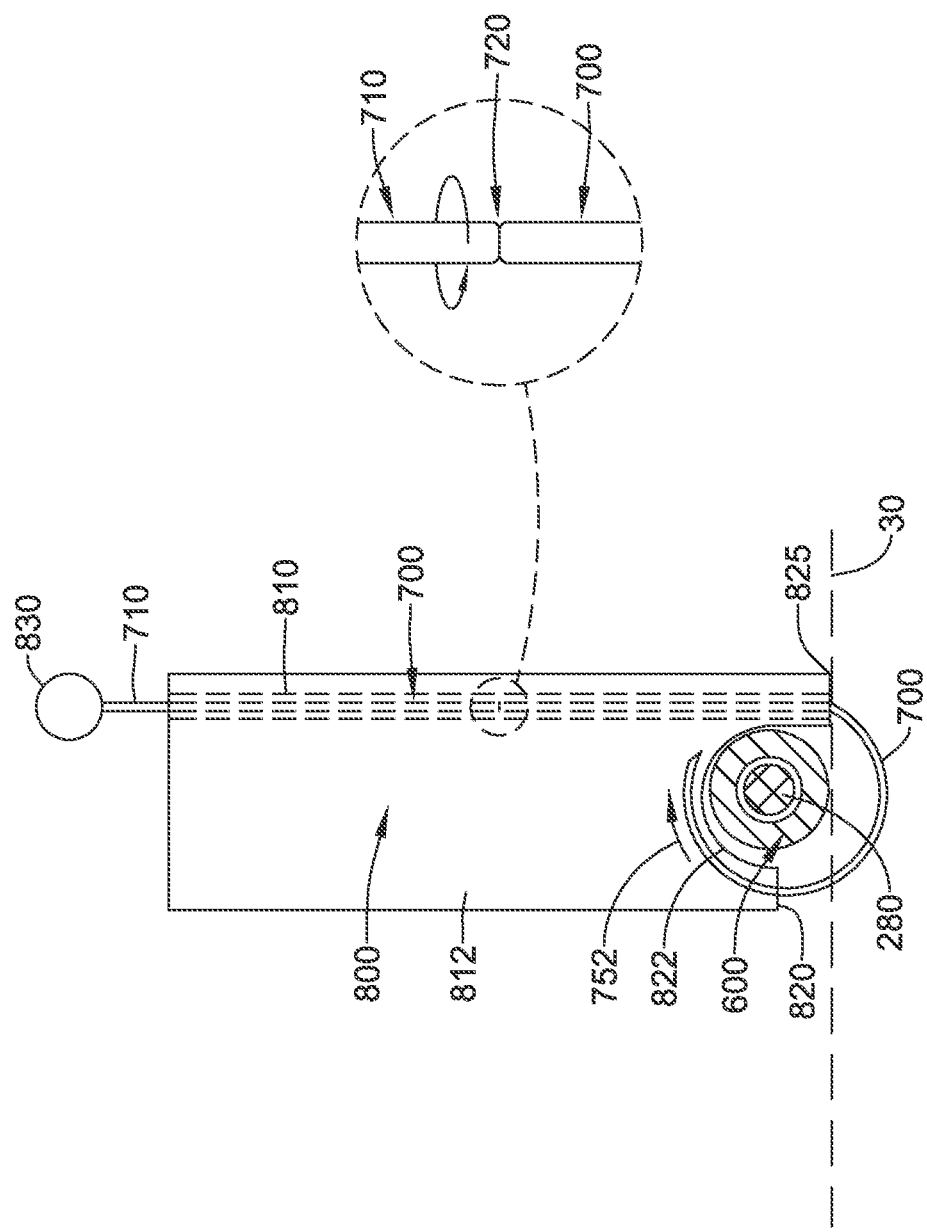
FIG. 10B is a side view of the insertion device of FIG. 10A with the helical coil in a further deployed state.

In other examples, the coil 700 is a shape set section of wire that is connected to a straight section of wire 710 at a breakaway notch 720, as shown in the enlargement in FIG. 10B. In this example, the actuator 830 may be connected to the straight section of wire 710. Once fully deployed, the actuator 830 may be turned, rotating the straight section of the wire 710 to break the wire at breakaway notch 720, separating the deployment device 800 from the implanted coil 700. In still other examples, the coil 700 may be formed as a series of shape set coils connected to teach other at breakaway notches. In this example, the deployment device 800 may carry multiple coils 700, allowing for multiple coils to be deployed using a single device 800, without having to reload. As each coil 700 is deployed, the actuator 830 may be rotated, breaking away the deployed coil from the remaining coils still within the channel 810 of the deployment device 800. In either above example, the coil removably fixed to the actuator 830 allows the coil 700 to be retracted and repositioned. The actuator 830 may be pulled upwards, unwinding the coil 700 from around the suture sleeve 600. Once the coil 700 is positioned in the desired location, the actuator 830 is turned, breaking the connection between the coil and actuator 830, leaving the coil 700 implanted around the suture sleeve 600 and lead 280.

Figure 11:
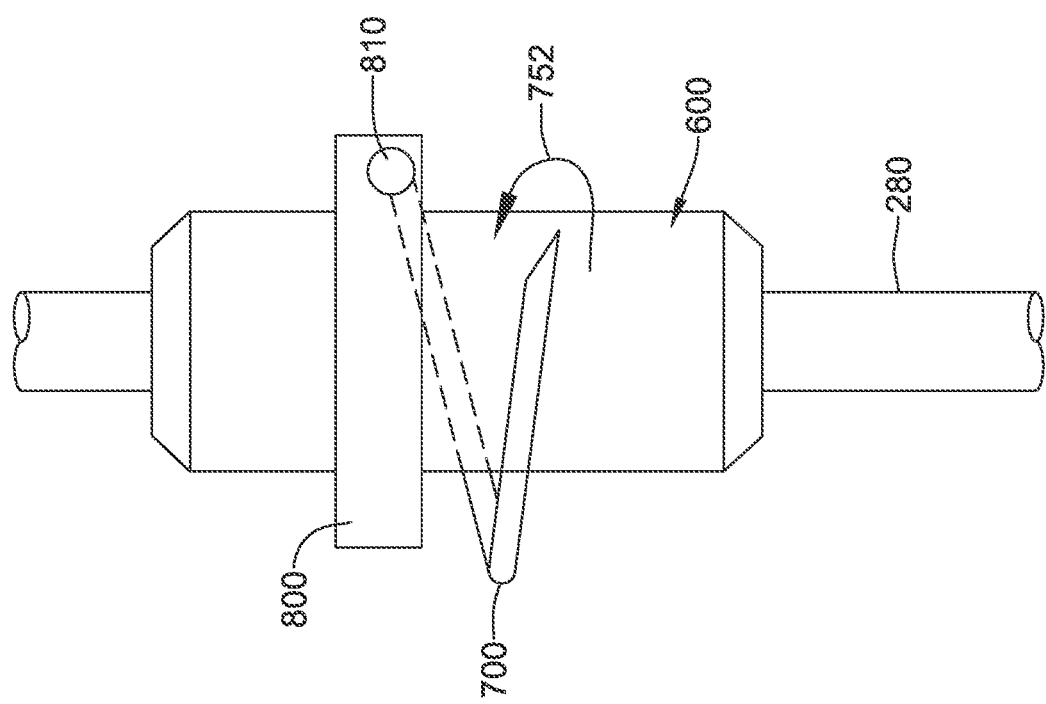
FIG. 11 is a top view of the insertion device of FIGS. 10A-10B with the helical coil partially deployed over the lead.

Regardless of how the coil 700 is pushed out of the deployment device 800, as the coil 700 continues to extend from the bottom of the channel 810, the end 742 of the coil 700 penetrates the fascial plane 30 at a location spaced apart from the first penetration location each time the coil extends around the suture sleeve 600, due to the helical geometry of the coil. FIG. 11 is a top view of the deployment device 800 showing the helical movement of the coil 700 as it is deployed. In some examples, the end 742 may be pointed or sharpened to facilitate penetration of the coil 700 into tissue. Alternatively, the end 742 may be angled, as shown in FIG. 10A. The angled end 742 may be positioned pointing away from or towards the suture sleeve 600. As shown in FIGS. 10B and 11, the coil 700 encircles the suture sleeve 600 and lead 280, securing them against the fascial plane 30. The coil 700 extends into and then out of the fascial plane 30 at least once, thereby securing the lead 280 to the fascial plane 30.

FIG. 12 is a side view of the helical coil 700 showing multiple turns. The helical coil 700 may define, one, two, three, or more complete turns. In some examples, the multiple turns have varying diameters. In the example shown in FIG. 12, the initial turn (on the left in the figure) has a first diameter D that is larger than the diameters of the remaining coils. The first diameter D of the coil 700 may match the diameter OD of the suture sleeve 600 to guide the helical coil 700 as it is deployed. The reduced diameter of additional coil turns provides compression (see FIG. 13), further securing the lead 280 and suture sleeve 600 to the fascial plane 30.

In some examples, the coil 700 may be made of a superelastic shape memory material, including metal and polymer shape memory materials. In one example, the coil 700 is nitinol. The coil 700 may be a wire having a diameter similar to that of conventional sutures. The coil 700 allows for securing leads and other medical devices without the use of a conventional suturing process. A coil 700 may be preloaded into the deployment device 800 providing advantages of being fast and easy to use, greatly reducing the procedure time as compared to securing a lead using conventional sutures. The coil 700 may secure the lead 280 to the fascia in a similar manner and location compared to conventional sutures, but is faster and may be used in smaller incisions as compared to those needed for manipulation of sutures. The incision may be 1 cm or less.

Some embodiments of the present invention may take the form of an implantation tool set configured for use in the subcutaneous implantation of one or more medical devices, such as electrode leads. The tool set may include an insertion device and one or more retainer clips or coils.

The various components of the devices/systems disclosed herein may include a metal, metal alloy, polymer, a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers for use in the leads discussed above may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS A), polycarbonates, ionomers, biocompatible polymers, other suitable materials, or mixtures, combinations, copolymers thereof, polymer/metal composites, and the like.

In at least some embodiments, portions or all of the accessory devices and their related components may be doped with, made of, or otherwise include a radiopaque material. Radiopaque materials are understood to be materials capable of producing a relatively bright image on a fluoroscopy screen or another imaging technique during a medical procedure. This relatively bright image aids the user of the accessory devices and their related components in determining its location. Some examples of radiopaque materials can include, but are not limited to, gold, platinum, palladium, tantalum, tungsten alloy, polymer material loaded with a radiopaque filler, and the like. Additionally, other radiopaque marker bands may also be incorporated into the design of the accessory devices and their related components to achieve the same result.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure, and shall not be used to interpret or limit the scope or meaning of the claims.

Various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A retainer clip configured to secure an electrode within a patient's body, comprising:
    first and second arms connected by a flexible bridge, the retainer clip configured to move between a first orientation in which lower surfaces of the first and second arms face each other, and a second orientation in which the first and second arms extend laterally from opposite sides of the flexible bridge in which lower surfaces of the first and second arms no longer face each other, wherein the retainer clip is biased in the second orientation;
    wherein the second orientation is a deployed configuration adapted to secure a lead carrying the electrode beneath the flexible bridge as the first and second arms extend laterally therefrom to secure the lead in place.

2. The retainer clip of claim 1, wherein the flexible bridge extends outward from an upper surface of the first and second arms, transverse to a plane of the first and second arms.

3. The retainer clip of claim 2, wherein:
    the first and second arms have a first width greater than a width of the flexible bridge;
    first ends of the first and second arms are attached to the flexible bridge and second ends of the first and second arms are tapered to a second width less than the first width; and
    a cross-section taken along a longitudinal axis of the retainer clip extending between second ends of the first and second arms defines at least one curve.

4. The retainer clip of claim 1, wherein the first and second arms have a plurality of protrusions extending outward from the lower surfaces.

5. The retainer clip of claim 4, wherein the protrusions on the first and second arms extend at an angle toward the flexible bridge.

6. The retainer clip of claim 4, wherein the protrusions are formed from curved or V-shaped cuts through the first and second arms and bending a portion of each arm adjacent the cuts downward away from an upper surface of the first and second arms.

7. The retainer clip of claim 1, wherein the flexible bridge is sized and configured to partially surround an electrode.

8. The retainer clip of claim 7, wherein the flexible bridge is C-shaped, the flexible bridge having a back side opposite an opening defining the C, the opening sized and configured to receive an electrode.

9. The retainer clip of claim 8, wherein:
the first and second arms are attached to the back side of the flexible bridge; and
the first and second arms are a single monolithic structure attached to the back side of the flexible bridge.

10. The retainer clip of claim 8, wherein the first and second arms are attached to opposite sides of the flexible bridge between the back side and the opening.

11. The retainer clip of claim 1, wherein when the first and second arms are in the second configuration, the lower surfaces of the first and second arms each face the same direction.

12. A retainer clip and delivery device assembly, comprising:
a retainer clip including first and second arms connected by a flexible bridge, the retainer clip configured to move between a first orientation in which lower surfaces of the first and second arms face each other, and a second orientation in which the first and second arms extend laterally from opposite sides of the flexible bridge and no longer face each other, wherein the retainer clip is biased in the second orientation, and wherein the second orientation is a deployed configuration adapted to secure a lead beneath the flexible bridge as the first and second arms extend laterally therefrom to secure the lead in place; and
a delivery device including a housing and a plunger, the housing having a lumen configured to receive the retainer clip in the first orientation, the plunger slidingly engaged within the lumen; wherein the retainer clip is delivered by sliding the plunger through the lumen, moving the retainer clip out of the delivery device.

13. The retainer clip and delivery device assembly of claim 12, wherein the housing and the plunger each have a recess on a bottom surface thereof, positioned such that when the plunger is slid into the housing and the bottom surfaces of the housing and plunger are adjacent each other, the recesses are aligned.

14. The retainer clip and delivery device assembly of claim 12, wherein when the first and second arms are in the second configuration, the lower surfaces of the first and second arms each face the same direction.

15. A method of securing a lead subcutaneously within a patient, the method comprising:
with the lead exposed at an incision, placing a delivery device including a housing and a plunger over the lead, with the housing constraining a retainer clip in a first orientation, the retainer clip including first and second arms connected by a flexible bridge, the retainer clip configured to move between the first orientation in which lower surfaces of the first and second arms face each other, and a second orientation in which the first and second arms extend laterally from opposite sides of the flexible bridge and no longer face each other, wherein the retainer clip is biased in the second orientation, and the second orientation is a deployed configuration adapted to secure the lead beneath the flexible bridge as the first and second arms extend laterally therefrom to secure the lead in place; and
depressing the plunger to release the retainer clip, thereby allowing the retainer clip to return to the second orientation, with the arms of the retainer clip engaging tissue on either side of the lead and the flexible bridge residing over the lead, wherein the lead is secured subcutaneously when the retainer clip is in the second orientation.

16. The method of claim 15, wherein the incision is 1 cm or less in length.

17. The method of claim 15, wherein securing the retainer clip includes snapping the flexible bridge over the lead.

18. The method of claim 15, wherein the lead includes one or more groove, and the step of depressing the plunger is performed such that the retainer clip, once released, engages the groove of the lead.

19. The method of claim 15 wherein, following the step of depressing the plunger, the lower surfaces of the first and second arms both face a fascial plane of the patient, thereby securing the lead in place.

* * * * *